United States Patent
Yagnik et al.

(10) Patent No.: US 8,833,137 B2
(45) Date of Patent: Sep. 16, 2014

(54) METHOD FOR ASSESSMENT OF FRICTION PROPERTIES OF FIBERS OR SUBSTRATES UPON MECHANICAL TREATMENT

(71) Applicant: The Procter & Gamble Company, Cincinnati, OH (US)

(72) Inventors: Chetan Kantilal Yagnik, Kobe (JP); Kumar Varoon, Minneapolis, MN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/856,868

(22) Filed: Apr. 4, 2013

(65) Prior Publication Data
US 2013/0233049 A1    Sep. 12, 2013

Related U.S. Application Data

(62) Division of application No. 12/546,853, filed on Aug. 25, 2009, now Pat. No. 8,429,963.

(60) Provisional application No. 61/189,958, filed on Aug. 25, 2008.

(51) Int. Cl.

| | | |
|---|---|---|
| *G01N 19/02* | (2006.01) | |
| *A61Q 5/02* | (2006.01) | |
| *A61Q 5/12* | (2006.01) | |
| *A61K 8/46* | (2006.01) | |
| *A61K 8/34* | (2006.01) | |
| *A61K 8/891* | (2006.01) | |
| *G06Q 99/00* | (2006.01) | |

(52) U.S. Cl.
CPC    *G01N 19/02* (2013.01); *A61Q 5/02* (2013.01); *A61Q 5/12* (2013.01); *A61K 8/463* (2013.01); *A61K 8/342* (2013.01); *A61K 8/891* (2013.01); *G06Q 99/00* (2013.01)
USPC .................................................. 73/9; 73/159

(58) Field of Classification Search
None
See application file for complete search history.

(56) References Cited

U.S. PATENT DOCUMENTS

| | | |
|---|---|---|
| 4,639,321 A | 1/1987 | Barrat |
| 6,817,222 B2 | 11/2004 | Day |
| 2002/0010556 A1 | 1/2002 | Marapane |
| 2009/0071228 A1 * | 3/2009 | Sherman et al. ................. 73/9 |

FOREIGN PATENT DOCUMENTS

| | | |
|---|---|---|
| CN | 1196442 | 12/2003 |
| CN | 1454310 A | 2/2004 |
| EP | 152194 | 1/1984 |
| EP | 413416 A | 9/1994 |
| JP | 62273433 A | 11/1987 |

OTHER PUBLICATIONS

Hiroshi Yagi & 4 Others, Research Study of a Friction Protector for Preventing a Tow Line From Breaking, Working Papers for Fiscal 2006, Japan, Japan Coast Guard, Dec. 2007, pp. 1-8.
Latorre Carmen, Nanotribological Effects of Hair Care Products and Environment on Human Hair Using Atomic Force Microscopy, Journal of Vacuum Science and Technology: Part A., USA, AVS/AIP, Jun. 28, 2005, V23 N4, pp. 1034-1045.

* cited by examiner

*Primary Examiner* — Andre Allen
(74) *Attorney, Agent, or Firm* — Linda M. Sivik

(57) ABSTRACT

Method for assessment of friction properties of fibers or substrate. The method is useful for assessing the degree of damage of hair fibers, for demonstrating the efficacy of a composition for minimizing the friction properties of fibers or substrate and/or for supporting advertising claims.

12 Claims, No Drawings

“METHOD FOR ASSESSMENT OF FRICTION PROPERTIES OF FIBERS OR SUBSTRATES UPON MECHANICAL TREATMENT

FIELD OF THE INVENTION

The present invention relates to a method for assessment of friction properties of fibers or substrate. The present invention is also useful for assessing the degree of damage of hair fibers. The present invention is particularly useful for demonstrating the efficacy of a composition for minimizing the friction properties of fibers or substrate. The present invention may be utilized for supporting advertising claims

BACKGROUND OF THE INVENTION

Fibers, e.g. mammal hairs, generate friction when they are mechanically treated, e.g. when they are combed, brushed or rubbed. The generation of friction varies depending on the properties the fibers, the state of the fibers. Usually, the smoother the fibers are and the lower the friction generated upon combing, brushing or rubbing. Likewise, untidy and/or entangled fibers tend to increase the friction generated upon mechanical treatment. The friction generated may also vary depending on the method used for mechanically treating the fibers, and/or the device used for mechanically treating the fibers. The friction generated may vary depending on the number of time and the frequency at which the fibers are combed, brushed or rubbed. The friction may also vary depending on the device used for mechanically treating the fibers, e.g. using a comb comprising close tines is likely to generate a higher friction than a comb comprising spaced tines.

Smoothness of hair is usually associated with the quality of hair but also their degree of damage. The smoothness of hair is reduced when hair are damaged. Hair may be damaged by excessive washing, by treating hair with an inappropriate hair care composition, by exposing them to detrimental environmental conditions, e.g. pollution, sun, rain. Hair may also be damaged following bleaching, perming and/or coloring. This reduction in smoothness is believed to result from changes in the structure of the cuticle, the outermost part of the hair fiber. The more damaged hair are and the more friction generated upon mechanical treatment. In contrast, treating hair with a hair care composition, particularly a hair conditioning composition, aims at increasing hair smoothness and at reducing the friction generated upon mechanical treatment. Reducing the friction generated upon mechanical treatment is preferable as it limits the damages induced by the mechanical treatment itself, i.e. by combing hair, and as it eases the experience of mechanically treating hair.

The consumers and/or users are concerned of having smooth and undamaged hair. The degree of damage may be merely assessed by consumers and/or users by looking and/or touching their hair. However, these methods are subjective and provide little information about the degree and the type of damage. The degree of smoothness may also be assessed by using a combing test in which the force required to detangle, by passing a comb device through hair, is assessed. The degree of damage may also be assessed by methods allowing inspection of hair structure, e.g. microscopy. The degree of damage may be also assessed by methods for assessing the friction properties of hairs. See for example U.S. Pat. No. 6,817,222. However, these methods usually require many types of equipment and provide data to be interpreted by the skilled person, while being barely understandable for consumers and/or users. In contrast, there is a need for a method allowing a direct visualization of the friction generated upon mechanical treatment. In other words, there is a need for a method allowing a direct visualization of the degree of hair damages.

In order to prevent and/or to treat hair damage, the consumers and/or users use hair care compositions. Hair care compositions may comprise many different types of components, e.g. conditioning agents. Hair care compositions may prevent hairs from being damaged, e.g. by exposure to detrimental environments. Hair care compositions may also repair damages by creating a protecting layer around hair. Consumers and/or users are usually interested in knowing whether hair compositions are efficient for preventing and/or treating hair damages. There is a need, therefore, for a method allowing an accurate assessment of the efficacy of a hair care composition for minimizing the friction generated upon mechanical treatment of hair, and so for preventing and/or treating hair damage. There is a need, also, for a method allowing a direct visualization of the efficacy of a hair care composition for minimizing the friction generated upon mechanical treatment of hair. In other words, there is a need for a method allowing a direct visualization of the efficacy of a hair care composition for preventing and/or treating hair damage.

Many different types of hair care compositions are available onto the market. Consumers and/or users are interested in understanding and selecting the compositions having the greater efficacy for preventing and/or treating hair damage. There is a need, therefore, for a method allowing an accurate comparison between the efficacy of hair care compositions for minimizing the friction generated upon mechanical treatment of hair, and so for preventing and/or treating hair damages. There is a need, therefore, for a method for comparing the efficacy of hair care compositions for minimizing the friction generated upon mechanical treatment of hair. In other words, there is a need for a method for comparing the efficacy of hair care compositions for preventing and/or treating hair damages.

In addition, there is a need for a method which can be easily understood by the non-skilled person, including the consumer and/or the end user. There is also a need for a method for supporting advertising claims about the efficacy of a hair care composition for minimizing the friction generated upon mechanical treatment of hair and, therefore, for preventing and/or treating hair damages. There is also a need for a method for supporting advertising claims about the comparison of the efficacy of at least two hair care compositions for minimizing the friction generated upon mechanical treatment of hair and, therefore, for preventing and/or treating hair damages. Finally, there is a need for a method of marketing a hair care composition, which composition is capable of minimizing the friction generated upon mechanical treatment of hair and, therefore, is capable of preventing and/or treating hair damages.

SUMMARY OF THE INVENTION

In a first aspect, the present invention relates to a method for assessment of friction properties of fibers or substrate, comprising the steps of:
  providing one sample of at least one fiber or substrate;
  mechanically treating at least one part of the sample by a method generating friction using a friction device; and,
  assessing the temperature of the sample and/or the friction device after mechanically treating at least part of the sample using a temperature sensor.

In a preferred aspect, the method further comprises the steps of:
  converting the temperature data to a color signal; and,
  displaying the color signal using a display device.

In another preferred aspect, the method further comprises the step of treating the sample with a composition, which composition is capable of minimizing the friction properties of fibers or substrate when mechanically treated.

In another preferred aspect, the method further comprises the step of providing at least one additional sample of at least one fiber or substrate.

In a second aspect, the present invention relates to a method for demonstrating the efficacy of a hair care composition, which composition is capable of minimizing the friction properties of hairs upon mechanical treatment, said method comprising the steps of:
- providing a first and a second sample of hair;
- treating the first sample with a hair care composition;
- assessing the temperature of the samples and/or the combs before combing at least part of the samples using a temperature sensor;
- mechanically treating the first and the second samples using a comb;
- assessing the temperature of the samples and/or the combs after mechanically treating the samples using a temperature sensor;
- assessing the temperature differential of each sample and/or comb before and after combing at least part of the sample;
- comparing the temperature differentials of the first and the second samples and/or the combs.

In a third aspect, the present invention relates to a method for marketing a hair care composition for demonstrating the efficacy of a hair care composition, which composition is capable of minimizing the friction properties of hairs upon mechanical treatment, said method comprising the steps of:
(1) offering for sale said hair care composition,
(2) advertising the efficacy of the hair care composition for minimizing the friction properties of hairs upon mechanical treatment providing at least one sample of hair and/or for preventing and/or treating hair damages;
(3) demonstrating said efficacy by conducting a method comprising the steps of;
   (a) providing at least one sample of hair;
   (b) assessing the temperature of the sample and/or the comb before combing at least part of the sample using a temperature sensor;
   (c) mechanically treating the sample using a comb;
   (d) assessing the temperature of the sample and/or the comb after mechanically treating the samples using a temperature sensor;
   (e) assessing the temperature differential of sample and/or comb before and after combing at least part of the sample;
   (f) converting the temperature data obtained at steps (b), (d) and (e) to a color signal;
   (g) displaying the color signals using a display device.

DETAILED DESCRIPTION OF THE INVENTION

The present invention relates to a method for assessment of friction properties of a sample of at least one fiber or substrate, after mechanically treating at least part of the sample using a friction device, by assessing the temperature of the sample and/or the friction device using a temperature sensor. The invention may be useful to assess the degree of hair damage. The invention may also be useful to demonstrate the efficacy of a hair care composition for preventing and/or treating hair damage. The invention may also be useful to compare the efficacy of at least two hair care compositions for preventing and/or treating hair damage. The invention may also be useful for marketing a hair care composition.

The inventors have found that friction properties of fibers, e.g. mammal hair, can be assessed by a method comprising the step of assessing the temperature of the sample and/or the friction device, after mechanically treating at least part of this sample, using a temperature sensor. Specifically, the inventors have found that the temperature of hair and/or the friction device is correlated to the friction generated upon mechanical treatment, and therefore it is correlated to the degree of hair damage. The higher the friction upon mechanical treatment is, the higher the increase of the temperature of hair and/or the temperature of the friction device after mechanical treatment. Friction properties of hair are correlated to the resistance of hair against combing, brushing and/or rubbing. Part of the energy that is generated by friction between hair and the friction device, e.g. a comb, is dissipated as heat. The dissipation of heat induces, therefore, an increase of the temperature at the point of contact where the friction occurs.

The inventors have also found that this method may be useful for supporting advertising claims. When the or at least one sample is treated with a composition, the method is useful for demonstrating the efficacy of the composition for minimizing the friction properties of fibers or substrate when mechanically treated. This demonstration is useful for supporting advertising claims about the efficacy of this composition for minimizing the friction properties of fibers or substrate when mechanically treated and/or for marketing this composition. More generally, the method is useful for demonstrating the efficacy of the composition for preventing and/or treating hair damages and the demonstration may be utilized for supporting advertising claims about the efficacy of this composition for preventing and/or treating hair damages. Particularly, the inventors have found that this method allows the non-skilled person, i.e. the consumer and/or the end user, to easily assess the efficacy of a composition and to easily compare this efficacy with the efficacy of other compositions and/or with the absence of treatment, when displayed in an appropriate manner. Without wishing to be bound by any theory, it is believed that the consumer and/or the end-user, who is usually a non-skilled person, wishes the advertising claims to be proved/supported by experimental results. It is also believed that conducting this method in front of the consumer, as a live experiment or via a recorded film, may convince him/her of the efficacy of the composition and my convince him/her to buy and/or to use this composition.

When the or at least one sample of at least one fiber or substrate is treated with a composition, the method is useful for demonstrating the efficacy of the composition for minimizing the friction generated upon mechanical treatment. Consequently, the method is useful for demonstrating the efficacy of a hair care composition for preventing and/or treating hair damage. Without wishing to be bound by any theory, it is believed that temperature increase generated by mechanically treating hair is proportional to the degree of hair damage. It is also believed that the ability to minimize temperature increase, by minimizing the friction generated upon mechanical treatment, is directly correlated to the efficacy of a composition for preventing and/or treating hair damage.

The invention is also useful for comparing the efficacy of hair care compositions for minimizing the friction generated upon mechanical treatment. Consequently, the method is useful for demonstrating the efficacy of hair care compositions for preventing and/or treating hair damage. Without wishing to be bound by any theory, it is believed that the difference of temperature differential generated by mechanically treating hair between two samples treated with different hair care compositions is directly correlated to the difference of efficacy of these compositions for preventing and/or treating hair damages.

The method comprises the step of providing at least one sample of at least one fiber or substrate, preferably from one to five samples of at least one fiber or substrate, and more preferably one sample or two samples of at least one fiber or substrate.

As used herein, "fiber" means any fiber that is susceptible to generate friction upon mechanical treatment, e.g. upon combing, brushing and/or rubbing. Said fiber is preferably mammal hair, more preferably human, horse, cat, dog hair, still more preferably human hair. Said mammal hair may be a cut hair or it may be growing hair, e.g. hair growing on the head of a living being such as a human person. When mechanically treated, hair may generate friction, also called "friction force". Alternatively, said fiber may be any natural fiber or synthetic fiber that is susceptible to generate a friction upon mechanical treatment and that is used for various applications, including fabrics, textile, garment, nonwovens, paper.

As used herein, "substrate" means any fiber equivalent material that is susceptible to generate friction upon mechanical treatment. Said substrate is preferably a mammal hair equivalent material, more preferably a human hair equivalent material. For example, human hair equivalent material may be conventional artificial hair. Alternatively, said substrate may be selected from any natural, synthetic or composite substrate that is susceptible to generate a friction upon mechanical treatment and that is used for various applications, including fabrics, textile, garment, nonwovens, paper.

The or each sample of at least one fiber may comprise a multitude of fibers which are bundled together at one end. The or each sample is preferably suspended vertically with the free end of said fibers hanging down such that the fiber ends are all in substantially the same horizontal plane.

Said sample is preferably a strand of mammal hair. Said sample of hair have preferably a weight from 0.1 to 200 grams, more preferably from 2 to 50 grams, still more preferably from 4 to 20 grams. Said hair has also preferably a length from 1 cm to 150 cm, more preferably from 1 cm to 50 cm, still more preferably from 5 cm to 30 cm, and even more preferably from 6 cm to 12 cm. When it is provided at least two samples of hairs, these samples have the same number of individual hair with a deviation of +/−50%, preferably +/−30%, more preferably +/−10%, hair between samples.

The method also comprises the step of mechanically treating at least part of the sample by a method generating friction using a friction device. Preferably, the mechanical treatment of at least part of the sample is selected from combing, brushing, rubbing or combinations thereof. More preferably, the mechanical treatment of at least part of the sample is combing.

As used herein, "friction" (also called "friction force") means the resistance of the sample of at least one fiber and/or substrate, and/or the resistance of the friction device, against the mechanical treatment. When the fibers are hair or hair equivalent materials, the friction generated upon mechanical treatment such as combing, brushing and/or rubbing is also called the grooming force. Specifically, when the fibers are hair, the friction generated upon combing is called the combing force.

As used herein, "friction device" means a device generating friction between the friction device and the surface of the fibers or the substrate when the friction device contacts and passes over the surface of the fibers or the substrate. When the fibers are hair or hair equivalent materials, the friction device may be any suitable device for combing, brushing and/or rubbing hairs. For example, the friction device may be a comb, a brush or a rubber glove. Preferably, the friction device is a comb.

The sample may be treated mechanically entirely or partially. When the sample is a strand of mammal hair, hair may be treated mechanically on half of their length. A portion (or part) of hairs from 2 cm to 30 cm, preferably from 3 cm to 20 cm, more preferably from 5 cm to 10 cm, of mammal hair may be treated mechanically using a friction device.

The sample may be treated a sufficient number of time over a sufficient period of time in order to generate friction using a friction device. The sample is treated mechanically preferably from 1 to 100 times, more preferably from 1 to 50 times. The sample is treated mechanically preferably over a period of time from 1 sec to 120 sec, more preferably from 1 to 60 sec, still more preferably from 1 to 30 sec. The frequency of the mechanical treatment can be, for example, from 1 to 100 times per 30 seconds, preferably from 10 to 50 times per 30 seconds, more preferably from 20 to 40 times per 30 seconds.

The method also comprises the step of assessing the temperature of the sample of at least one fiber or substrate and/or the friction device, after mechanically treating at least part of the sample, using a temperature sensor.

As used herein, "temperature sensor" means any device suitable for detecting and assessing the temperature of an object and optionally recording the temperature data. Preferably, the temperature sensor, according to the present invention, is a device suitable for discriminating a low temperature variation, e.g. a temperature variation of about 0.01° C.

Preferably, the temperature is assessed by using a temperature sensor selected from temperature sensitive friction device, an infra-red camera, or combination thereof. More preferably, the temperature sensor is an infra-red camera.

A temperature sensitive friction device may be a device made, at least partially, of a temperature sensitive material. A temperature sensitive material may be a material changing its appearance, e.g. its color, depending on its temperature. A temperature sensitive material may be a material changing its state, e.g. from solid to liquid or from liquid to gaseous, depending on its temperature. A temperature sensitive material may be mercury.

Any infra-red camera suitable for discriminating a low temperature variation may be used. For example, the camera LAIRD-S270A® supplied by Nikkon may be used.

The temperature may be assessed from 1 sec to 1 h, preferably from 1 sec to 10 min, more preferably from 1 sec to 1 min, after mechanically treating the sample.

The method comprises the step of assessing temperatures ranges preferably from 15° C. and 50° C., more preferably from 20° C. to 40° C., still more preferably from 20° C. to 30° C.

The method may comprise the step of assessing the temperature of the sample and/or the friction device, using a temperature sensor, before mechanically treating at least part of the sample. When the temperature of the sample is assessed both before and after the mechanical treatment of the sample, the method may further comprise the step of assessing the difference of temperature of the sample and/or the friction device before and after mechanically treating at least part of the sample.

The difference of temperature, also called "temperature differential", may be correlated with a specific degree of friction. For example, temperature differentials of 0.1° C., 0.5° C. and 1.5° C. may be correlated respectively as low, medium and high degree of friction. The correlation between the temperature differential and the degree of friction may differ depending on the fiber and/or substrate used. It may also depend on the friction device used.

When assessing friction properties of hair fibers or hair equivalent material, the difference of temperature may be correlated with a specific degree of hair damage. For example, temperature differentials of 0.1° C., 0.5° C. and 1.5°

C. may be correlated respectively as low, medium and high degree of hair damage. The correlation between the temperature differential and the degree of hair damage may differ depending on the fiber and/or substrate used. It may also depend on the friction device used.

The temperature may be assessed from 1 sec to 1 h, preferably from 1 sec to 10 min, more preferably from 1 sec to 1 min, before mechanically treating the sample.

The temperature differential ranges may vary depending on the sample used, and/or the friction device used and the parameters of the method.

The method may also comprise the step of assessing the temperature of the sample and/or the friction device during mechanically treating at least part of the sample using a temperature sensor. The temperature may be assessed continuously from the beginning to the end of the mechanical treatment. Alternatively, the temperature may be assessed sequentially, e.g. every second, from the beginning to the end of the mechanical treatment. Assessing the temperature, not only before and/or after the mechanical treatment, but also during the mechanical treatment is useful in order to assess the change of temperature, and so to assess the generation of friction, induced by the mechanical treatment over time.

The method may comprise the step of converting temperature data to a signal that may be recorded and/or displayed using a display device. This signal is called herein "the temperature signal". The method may also comprise the step of displaying this temperature signal using a display device. The conversion of temperature data to a displayable temperature signal may be achieved using known means.

The temperature data may be converted as a continuous temperature signal recorded over a determined period of time. Alternatively, the temperature may be converted as a multitude of temperature signals recorded at determined intervals over a determined period of time.

The display of the temperature signal may be substantially instantaneous so that the display of the temperature signal using a display device is displayed at the same time as the sample of at least one fiber and/or substrate is mechanically treated using a friction device. The display of the temperature signal may also be delayed in time.

The display device may be a visual display unit, preferably a display screen. The display screen may be selected from a computer screen, a cathode ray tube device, a liquid crystal display device, or combinations thereof.

Preferably, temperature data is converted to a color temperature signal. The color temperature signal can be standardized so as to correspond to a determined temperature. For example, color temperature signals may correspond to a color scale ranging from blue color to red color and wherein the color is correlated with a low temperature increase while red color is correlated with a high temperature increase.

The conversion of the temperature data to a color temperature signal, its record and its display using a display device are particularly useful when the temperature is assessed before, during and after mechanically treating at least part of the sample.

The method may comprise the step of treating the sample with a composition, which composition is capable of minimizing the friction properties of fibers or substrate when mechanically treated with a method generating friction using a friction device. Such compositions are called herein "treating compositions". Preferably, the composition is a hair care composition. More preferably, the composition is a composition selected from shampoo, hair conditioning composition, hair styling composition, or combinations thereof. Still more preferably, the composition is a hair conditioning composition.

As used herein, "conditioning composition" means a composition comprising at least one conditioning active agent. The conditioning agent may be selected from any conventional conditioning agent, including some silicone components, some fatty alcohol, etc. Suitable examples of hair conditioning agents may be found in the CFTA International Cosmetic Ingredient Dictionary and Handbook, $11^{th}$ edition, 2006.

The sample is preferably treated with 0.01 ml to 1 ml, more preferably 0.05 ml to 0.5 ml, of composition by gram of sample.

Alternatively, the method may comprise the step of treating the sample with a composition, which composition is capable of increasing the friction properties of fibers or substrate when mechanically treated with a method generating friction using a friction device. Such composition may be useful when using fibers or substrates used for various applications, including fabrics, textile, garment, nonwovens, and paper.

The method may comprise the step of providing at least one additional sample of at least one fiber or substrate.

When it is provided at least one additional sample, this method may also comprise the steps of:
  mechanically treating at least part of the or each additional sample by a method generating friction using a friction device;
  assessing the temperature of the or each additional sample and/or the friction device, after mechanically treating at least part of the or each additional sample, using a temperature sensor; and,
  comparing the temperature of all samples and/or all friction devices after mechanically treating at least part of the samples.

When it is provided at least one additional sample, this method may also comprise the steps of:
  assessing the temperature of the samples and/or the friction devices before mechanically treating at least part of the sample;
  assessing the temperature differential of each sample and/or each friction device before and after mechanically treating at least part of the sample;
  comparing the temperature differentials for all samples and/or all friction devices.

When it is provided at least one additional sample, this method may also comprise the steps of assessing the temperature of each sample and/or the friction devices during mechanically treating at least part of these samples using a temperature sensor.

Providing at least one additional sample—and then mechanically treating each sample, assessing the temperature of each sample and/or each friction device and comparing the temperature differentials between all samples and/or all friction devices—may be useful to compare the friction properties of the samples.

In one embodiment, the samples used may be different from each other. The samples may be strands of mammal hair from different origins, e.g. oriental hairs versus Caucasian hairs. The samples may also be strands of mammal hairs having been chemically treated in different ways, e.g. untreated hairs versus bleached hairs and/or dyed hairs.

In another embodiment, the samples may be treated with different compositions being capable of minimizing the friction properties of fibers or substrate, e.g. untreated hairs versus hairs treated with a hair conditioning composition. When different compositions are used, it is preferable all samples to be substantially identical to each other, i.e. same origin and substantially the same weight, length and number.

In still another embodiment, the samples may be mechanically treated using different friction devices, e.g. hairs treated with a comb with close tines versus hairs treated with a comb with large space in-between; and/or hairs treated with a comb made of rubber versus hairs treated with a comb made of steel. When different frictions are used, it is preferable all samples to be substantially identical to each other, i.e. same origin and substantially the same weight, length and number.

As a general matter, in order to improve the comparability of the temperature data obtained, it is usually preferable to modify only one parameter—e.g. different samples; treatment with different compositions being capable of minimizing the friction properties of the fibers or substrate; different friction devices. Consequently, all other experimental conditions and parameters are preferably substantially identical.

When it is provided at least one additional sample, it is provided preferably from 2 to 10 samples in total, more preferably from 2 to 5 samples in total, still more preferably 2 samples in total.

When it is provided at least one additional sample, the methods for assessment of friction properties of fibers or substrates may be conducted simultaneously or successively.

When conducted simultaneously, the steps of mechanically treating all samples are conducted substantially at the same time. The steps of assessing the temperature of all samples, and the optional step of comparing the temperature differentials, are conducted substantially at the same time. So as to facilitate the comparison between all samples, it may be advantageous to place all samples side-by-side. The distance between two samples may be sufficient to allow an easy comparison between the samples without altering the friction generation. When it is provided samples of mammal hairs bundled together at one end, it may be advantageous to place the vertically-suspended samples side-by-side.

When conducted successively, it is preferably conducted first the steps of mechanically treating the first sample and assessing the temperature of this sample and/or the friction device. Then, it is conducted the steps of mechanically treating the second sample and assessing the temperature of this second sample and/or the friction device. Then, it is conducted the steps of mechanically treating any additional sample and assessing the temperature of this sample and/or the friction device. It may be advantageous to record the temperature data obtained for each sample in order to allow the comparison of these data between each other after assessing the friction properties of all samples and/or friction devices.

In a preferred embodiment, the steps of providing the or each sample and/or the step of mechanically treating the or each sample may be recorded using a recording device as a signal that may be displayed using a display device. The recording device may be a camera.

These steps may be recorded as a continuous signal, e.g. as a film, over a determined period of time and/or they may be recorded as a multitude of signals, e.g. as pictures, at determined intervals over a determined period of time. For example, it may be taken pictures every 10 sec.

The display device may be a visual display unit, preferably a display screen, as detailed above.

The record and the display of the signal, e.g. the film or pictures, may be substantially instantaneous so that the display of the signal using a display device is displayed at the same time as the or each sample being provided and mechanically treated. The display of the signal may also be delayed in time.

When the steps of providing and mechanically treating the or each sample are recorded to a signal that may be displayed using a display device and when the temperature data is also converted as a temperature signal that may be displayed using a display device, it may be advantageous to display both signals at the same time.

In a preferred embodiment, such simultaneous displays may be achieved using an IR camera in association with an appropriate device for converting the temperature data to a displayable temperature signal, e.g. a color temperature signal, and an appropriate display device. The IR camera allows both the filming of the steps of providing and mechanically treating the or each sample as well as the assessment of the temperature of the or each sample and/or the or each friction device. Using an IR camera is particularly advantageous as it allows the continuous assessment of the temperature before, during and after the mechanical treatment of the or each sample.

When using a display screen, the color temperature signal may be displayed in different ways used in isolation or in combination.

The color temperature signal may be displayed on screen as a numerical value expressed in appropriate units, e.g. degree Celsius or degree Fahrenheit.

The color temperature signal may also be displayed on screen using a color scale corresponding to a temperature range, e.g. color scale ranging from blue color (lower limit of the temperature range) to red color (of the temperature range), comprising a means indicating the color temperature signal. The means indicating the color temperature signal may be a cursor sliding along this scale. When the temperature of the sample and/or the friction device increases upon mechanical treatment of the sample with this friction device, the cursor slides proportionally along the color scale from the blue color towards the red color.

The color temperature signal may also be superimposed onto the part of the or each mechanically-treated sample and/or onto the or each friction device. Consequently, the sample and/or the friction device are displayed on screen with a specific color. Preferably, the color temperature signal is standardized so that a temperature range is correlated to a determined color scale. If the color scale ranges from blue color (lower limit of the temperature range) to red color (of the temperature range), then the sample and/or the friction device may be displayed as a blue-colored sample and/or friction device before being mechanically treated and, as the temperature of the sample and/or the friction device increases during the mechanical treatment upon generation of friction, the color of the sample and/or the friction device may change towards the red color. This way of displaying the color temperature signal is an easy and accurate way to visualize the increase of temperature upon mechanical treatment.

Using superimposition of the color temperature signal onto the sample and/or the friction device is particularly useful when it is provided at least two samples being placed side-by-side and being treated simultaneous. If the samples are different and/or if they have been treated with different compositions being capable of minimizing their friction properties of the sample and/or if the samples have been mechanically treated with different friction device, the change of color of the samples and/or friction devices will be easily comparable by visual inspection. A noticeable difference of color between the samples and/or the friction devices at the same time of the mechanical treatment is easily understood as a difference of temperature, and therefore, as a difference of friction properties between the samples.

For example, when it is provided two samples of hairs (one sample being untreated while the other sample being treated with a hair care composition), the visual inspection and the comparison of the color change of the samples and/or the friction devices allows an easy and accurate understanding about the change of temperature of the samples and/or the friction devices. If the color change of the untreated sample towards the red color upon mechanical treatment is significantly faster than the color change of the treated sample, this is an accurate indication that the hair care composition effectively minimizes the friction properties of the sample and, therefore, limits the temperature increase upon mechanical treatment. As the minimization of the friction properties of hair is correlated with the prevention and/or treatment of hair damage, this is an accurate indication that the hair composition effectively prevents and/or treats hair damage.

For example, when it is provided two samples of hairs treated with two different hair care compositions, the visual inspection and the comparison of the color change of the samples and/or the friction devices allows an easy and accurate understanding about the change of temperature of the samples and/or the friction devices. If the color change of the first treated sample towards the red color upon mechanical treatment is significantly faster than the color change of the second treated sample, this is an accurate indication that the second composition minimizes further the friction properties of the sample compared to the first composition and, therefore, limits further the temperature increase upon mechanical treatment. As a further minimization of the friction properties of hair is correlated with an increased prevention and/or treatment of hair damage, this is an accurate indication that the second composition has a better efficacy for preventing and/or treating hair damages.

The method may also comprise the step of utilizing the assessment and/or the comparative assessment to support advertising claims. This is particularly advantageous when the method is displayed to the non-skilled person, preferably the consumer and/or the end-user, in association with advertising claims.

Preferably, the method is recorded and incorporated, in combination with the advertising claims, into a commercial, which commercial is capable to be displayed onto any image diffusion support, e.g. television screen, computer screen, theatre screen, in-store screen accessible to the consumer and/or the end-user.

When the method is recorded, it may not be necessary to record the step of treating the, at least one or each sample with a composition. Instead, it may be recorded the step of indicating that the, at least one or each sample has been treated previously with a composition.

In a second aspect, the present invention relates to a method for demonstrating the efficacy of a hair care composition, which composition is capable of minimizing the friction properties of hairs upon mechanical treatment, said method comprising the steps of:
  providing a first and a second sample of hair;
  treating the first sample with a hair care composition;
  assessing the temperature of the samples and/or the combs before combing at least part of the samples using a temperature sensor;
  mechanically treating the first and the second samples using a comb;
  assessing the temperature of the samples and/or the combs after mechanically treating the samples using a temperature sensor;
  assessing the temperature differential of each sample and/or comb before and after combing at least part of the sample;
  comparing the temperature differentials of the first and the second samples and/or the comb.

The second sample may be treated with a different hair care composition or, alternatively, the second sample may not be treated.

In a third aspect, the present invention relates to a method for marketing a hair care composition for demonstrating the efficacy of a hair care composition, which composition is capable of minimizing the friction properties of hairs upon mechanical treatment, said method comprising the steps of:
  (1) offering for sale said hair care composition;
  (2) advertising the efficacy of the hair care composition for minimizing the friction properties of hairs upon mechanical treatment providing at least one sample of hair and/or for treating and/or preventing hair damages;
  (3) demonstrating said efficacy by conducting a method comprising the steps of;
    (a) providing at least one sample of hair;
    (b) assessing the temperature of the sample and/or the comb before combing at least part of the sample using a temperature sensor;
    (c) mechanically treating the sample using a comb;
    (d) assessing the temperature of the sample and/or the comb after mechanically treating the samples using a temperature sensor;
    (e) assessing the temperature differential of sample and/or comb before and after combing at least part of the sample;
    (f) converting the temperature data obtained at steps (b), (d) and (e) to a color signal; and,
    (g) displaying the color signals using a display device.

EXAMPLES

The following example further describes and demonstrates the preferred embodiments within the scope of the present invention. This example is given solely for the purpose of illustration, and it is not to be construed as limitations of the present invention since many variations thereof are possible without departing from its scope.

Samples of oriental virgin round human hair are provided. The samples are strands of hair having a weight of about 2 grams (total weight) and a length of about 15 cm. The experiment is conducted in a chamber with controlled temperature and humidity, where the temperature is about 23° C. and the relative humidity is about 45% RH.

Step A—The first sample is treated with the non-conditioning shampoo comprising about 33% of surfactants, i.e. ammonium laureth sulfate, ammonium lauryl sulfate, cocamide DEA and ammonium xylene sulfonate, in a aqueous carrier. This first sample is the control sample, i.e. the sample not treated with a conditioning component. The sample is hung above the sink and the water is adjusted to a temperature of 38° C. and a pressure of 1.5 gpm. The sample is wet thoroughly for 15 seconds and then 0.2 cc of the composition is applied evenly down the sample. The composition is milked onto hair for 30 seconds, using thumb and forefinger. Then, the sample is rinsed with water for 30 seconds by supporting the back of the sample with one hand, allowing water to pulse down the entire sample. The steps of applying the composition, milking the composition and rinsing the composition are repeated once more. Excess water is squeezed out. Then, the sample is let drying overnight in the chamber at a temperature of about 23° C. and in a relative humidity of about 45% RH.

Step B—The second sample is treated with a conditioning shampoo comprising about 16% surfactants, i.e. ammonium laureth sulfate and ammonium lauryl suflate, and about 1.1% conditioning components, i.e. cetyl alcohol and dimethicone. This conditioning shampoo is called herein "conditioning composition (1)". This second sample is the treated sample (1), i.e. the sample treated with the conditioning composition (1). The sample is hung above the sink and the water is adjusted to a temperature of 38° and a pressure of 1.5 gpm. The sample is wet thoroughly for 15 seconds and then 0.1 cc of conditioning composition (1) is applied evenly down the sample. The composition is milked for 30 seconds by using thumb and forefinger. Then, the treated sample (1) is rinsed with water for 30 seconds by supporting the back of the sample with one hand, allowing water to pulse down entire sample. Excess water is squeezed out. Then, the sample is let drying overnight in the chamber at a temperature of about 23° C. and in a relative humidity of about 45% RH.

Step C—The third sample is treated with a conditioning shampoo comprising about 14% surfactants, i.e. ammonium laureth sulfate and ammonium lauryl suflate, and about 5.25% conditioning components, i.e. cetyl alcohol and dimethicone. This conditioning shampoo is called herein "conditioning composition (2)". This third sample is the treated sample (2), i.e. the sample treated with a conditioning composition (2). The sample is hung above the sink and the water is adjusted to a temperature of 38° and a pressure of 1.5 gpm. The sample is wet thoroughly for 15 seconds and then 0.1 cc of conditioning composition is applied evenly down the sample. The composition is milked for 30 seconds by using thumb and forefinger. Then, the treated sample (2) is rinsed with water for 30 seconds by supporting the back of the sample with one hand, allowing water to pulse down entire sample. Excess water is squeezed out. Then, the sample is let drying overnight in the chamber at a temperature of about 23° C. and in a relative humidity of about 45% RH.

Step D—After overnight drying, each sample, which is formed of a multitude of hair being bundled altogether at the top end, is suspended vertically with the free bottom end of hair hanging down such that the hair ends are all substantially in the same horizontal plane.

Step E—The free bottom end of the sample is grasped firmly using thumb and forefinger, in order to keep hair tight and still.

Step F—A section of hair of 8 cm, located between the top end and the bottom end of the sample, is mechanically treated using a combing device. The combing device, also called "comb", is Krest 400 Cleopatra All Purpose Professional comb. This comb is made of nitrile rubber. The comb is passed through hair at the top of the section of the sample to be mechanically treated. Then, hair are combed from the top to the bottom of this section in about one seconds per comb step. The step of combing hair is repeated 10 times at an approximate frequency of 10 times per 10 seconds.

Step G—The temperature of the section of the sample being mechanically treated is assessed simultaneously to the mechanical treatment using the Infra-Red camera Nikon LAIRD-S270A®. IR camera is placed about 100 cm from the sample of hairs. The temperature is assessed over a range from 22.5° C. to 27.5° C. The temperature of the section of hair being combed increases gradually following each combing step. The temperature of hair is recorded continuously from about 1 min before starting combing hair to about 1 min after combing hair. Comparing the temperature of the section of hair combed, before the first combing step and after the last combing step, allows assessing the difference of temperature induced by mechanically treating hair and, consequently, the difference of temperature induced by the friction generated upon combing.

Step H—Temperature ranging from about 22.5° C. to 27.5° C. is correlated to a color scale miming the visible light spectrum (from blue to red colors). Using the IR camera, the change of temperature is observable directly by a change of color of hairs.

The steps of mechanically treating the control and the treated samples (steps D and E), as well as the steps of assessing the temperatures of the control and the treated samples (steps F to H), may be conducted simultaneously or separately. When conducted simultaneously, the control and the treated samples may be placed side-by-side in order to ease the comparison of the difference of temperature and/or the difference of color of the control and the treated samples.

The temperatures and the temperature differentials of the control sample, the treated sample (1) and the treated sample (2) are detailed in the table below.

|  | Temperature of sample before combing (° C.) | Temperature of sample after combing (° C.) | Temperature differential (° C.) |
|---|---|---|---|
| Control sample | 23.4 | 24.7 | 1.3 |
| Treated sample (1) | 23.4 | 23.9 | 0.5 |
| Treated sample (2) | 23.2 | 23.8 | 0.6 |

The temperature differential of the control sample is higher than the temperature differential of the treated sample (1) and the treated sample (2). This demonstrates that friction generated upon combing the treated samples of hair is minimized compared to the control sample. The treatment of hair with a conditioning composition tends to minimize the friction properties of hairs.

Step I—Step F was repeated once again.

Step J—The temperature of the comb is assessed before and after the mechanical treatment using the Infra-Red camera Nikon LAIRD-S270A®. IR camera is placed about 100 cm from the sample of hairs. The temperature is assessed over a range from 22.5° C. to 27.5° C. Comparing the temperature of the comb, before the first combing step and after the last combing step, allows assessing the difference of temperature induced by mechanically treating hair and, consequently, the difference of temperature induced by the friction generated upon combing.

Step K—Temperature ranging from about 22.5° C. to 27.5° C. is correlated to a color scale miming the visible light spectrum (from blue to red colors). Using the IR camera, the change of temperature is observable directly by a change of color of hairs.

The temperatures and the temperature differentials of the comb used for treating the control sample, the treated sample (1) and the treated sample (2) are detailed in the table below.

|  | Temperature of comb before combing (° C.) | Temperature of comb after combing (° C.) | Temperature differential (° C.) |
|---|---|---|---|
| Control sample | 22.8 | 23.7 | 0.9 |
| Treated sample (1) | 22.5 | 22.9 | 0.4 |
| Treated sample (2) | 22.8 | 23.0 | 0.2 |

The temperature differential of the comb (control sample) is higher than the temperature differential of the comb (treated sample (1)) and the comb (treated sample (2)). This demonstrates that friction generated upon combing the treated samples of hair is minimized compared to the control sample. The treatment of hair with a conditioning composition tends to minimize the friction properties of hairs.

Step F to H and/or steps I to K of the demonstration may be recorded and the videos and/or pictures obtained may be incorporated into a commercial.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessment of friction properties of mammal hair, comprising the steps of:
   providing one sample being a strand of mammal hair;
   combing and/or brushing at least part of the sample by comb and/or brush; and,
   assessing the temperature of the sample, comb, and/or brush using a temperature sensor, after combing and/or brushing;
   converting temperature data to a color signal; and
   displaying the color signal using a display device.

2. A method, according to claim 1, further comprising the steps of:
   assessing the temperature of the sample, comb and/or brush before combing and/or brushing using a temperature sensor; and
   assessing the temperature differential of the sample, comb and/or brush before and after combing and/or brushing.

3. A method, according to claim 1, further comprising the steps of assessing the temperature of the sample, comb, and/or brush using a temperature sensor during combing and/or brushing.

4. A method, according to claim 1, further comprising the steps of:
   providing at least one additional sample being a strand of mammal hair;
   combing and/or brushing at least part of the additional sample by comb and/or brush; and,
   assessing the temperature of the additional sample, comb, and/or brush, after combing and/or brushing, using a temperature sensor;
   comparing the temperature of all samples, comb and/or brush after combing and/or brushing.

5. A method according to claim 4, further comprising the steps of:
   assessing the temperature of the samples comb, and/or brush before combing and/or brushing;
   assessing the temperature differential of each sample, comb, and/or brush before and after combing and/or brushing;
   comparing the temperature differentials of all samples comb, and/or brush.

6. A method, according to claim 1, wherein the strand of mammal hair comprises a multitude of hair fibers which are bundled together at one end and the sample is suspended vertically.

7. A method, according to claim 1, wherein the strand of mammal hair has a weight from 0.1 grams to 200 grams, and a length from 1 cm to 50 cm.

8. A method, according to claim 1, comprising the step of treating the sample with a hair care composition, which composition is capable of minimizing the friction properties of mammal hair when combing and/or brushing.

9. A method, according to claim 1 wherein at least a part of the sample is combed, or brushed from 1 to 100 times for 1 sec to 120 sec.

10. A method, according to claim 1, wherein the temperature is assessed by using a temperature sensor selected from temperature sensitive friction device, an infra-red camera, or combination thereof.

11. A method, according to claim 10, wherein the temperature sensor is an infra-red camera.

12. A method, according to claim 1, wherein the temperature ranges from 15° C. to 50° C.

* * * * *